(12) United States Patent
Klaas et al.

(10) Patent No.: US 6,380,439 B1
(45) Date of Patent: Apr. 30, 2002

(54) SINGLE-STAGE METHOD FOR PRODUCING α-HYDROXY ETHERS BY OXIDIZING C=C-UNSATURATED COMPOUNDS WITH HYDROPEROXIDES

(75) Inventors: Mark Rüsch gen. Klaas, Münster; Siegfried Warwel, Aachen; Hans-Martin Zillmann, Münster; Klaus Kwetkat, Bergkamen, all of (DE)

(73) Assignee: RWE-DEA Aktiengesellschaft fur Mineraloel und Chemie, Hamburg (DE)

( * ) Notice: Subject to any disclaimer, the term of this patent is extended or adjusted under 35 U.S.C. 154(b) by 0 days.

(21) Appl. No.: 09/403,474

(22) PCT Filed: Mar. 20, 1998

(86) PCT No.: PCT/EP98/01632

§ 371 Date: Jan. 25, 2000

§ 102(e) Date: Jan. 25, 2000

(87) PCT Pub. No.: WO98/47844

PCT Pub. Date: Oct. 29, 1998

(30) Foreign Application Priority Data

Apr. 24, 1997 (DE) .......................................... 197 17 265
Aug. 20, 1997 (DE) .......................................... 197 36 121

(51) Int. Cl.[7] .............................................. C07C 41/03
(52) U.S. Cl. ........................ 568/589; 568/613; 568/615; 568/618; 568/619; 568/672; 568/678; 568/679; 568/680; 568/695; 560/179; 560/186; 560/187; 562/8; 562/20; 562/36
(58) Field of Search ................................. 568/589, 613, 568/615, 619, 672, 678, 679, 680, 695; 560/179, 186, 187; 562/8, 20, 36; 502/171, 161

(56) References Cited

U.S. PATENT DOCUMENTS 2,808,442 A    10/1957  Smith et al. ................. 260/611
5,420,313 A  *  5/1995  Cunnington et al. ........ 549/529
5,977,404 A    11/1999  Kwetkat et al. .............. 562/36

FOREIGN PATENT DOCUMENTS

DE  3829735     10/1988
EP  0554590 B1   2/1992
GB  1122800      8/1968
GB  2252556 A    8/1992

OTHER PUBLICATIONS

R.A. Sheldon, "Synthetic and Mechanistic Aspects of Metal–Catalysed Epoxidations with Hydroperoxides," *Journal of Molecular Catalysis* 7 No Month Provided (1980), pp. 107–126.
Ronald A. Wohl, "The Mechanism of the Acid–Catalyzed Ring Opening of Epoxides—A Reinterpretative Review," *Chimia* 28 No Month Provided (1974), pp. 1–5.
Paul G. Gassmann and Thomas L. Guggenheim, "Opening of Epoxides with Trimethylsilyl Cyanide to Produce Beta–Hydroxy Isonitiriles. A General Synthesis of Oxazolines and Beta–Amino Alcohols," *Journal of the American Chemical Society*, 104 No Month Provided (1982), pp. 5849–5850.
Von M. Bischoff, U. Zeidler, and H. Baumann, "Atheralkohole und Esteralkohole—neue Tensidrohstoffe auf der Basis von Olefinoxiden," *Fette, Seifen, Anstrichmittel* 79 No Month Provided (1977), pp. 131–135.
Yusuke Izumi and Kyoji Hayashi, "Efficient Catalysis of Heteropoly Acid for Alcoholysis of Epoxide," *Chemistry Letters* No Month Provided (1980), pp. 787–790.
Von Gary H. Posner, "Organic Reactions on Alumina–Surfaces," *Angew. Chem.* 90 No Month Provided (1978), pp. 527–536.
March, Advanced Organic Chemistry, Reactions, Mechanisms, & Structure, 3rd edition, p. 346, 1985.*

* cited by examiner

*Primary Examiner*—Rosalynd Keys
(74) *Attorney, Agent, or Firm*—Browning Bushman P.C.

(57) ABSTRACT

A single-stage method for producing α-hydroxy ethers by oxidizing olefinic substrates with organic hydroperoxides and opening the resultant oxirane ring by means of monovalent or polyvalent alcohols wherein a molybdenum compound in combination with a compound selected from the group consisting of boron trifluoride, aluminum oxides, 1,8-diazabicyclo-[5.4.0]-undec-7-ene or 1,4-diazabicyclo-[2.2.2]-octane, and mixtures thereof is used as a catalyst system.

1 Claim, No Drawings

SINGLE-STAGE METHOD FOR PRODUCING α-HYDROXY ETHERS BY OXIDIZING C=C-UNSATURATED COMPOUNDS WITH HYDROPEROXIDES

This application is a 371 of PCT/EP98/01632 filed Mar. 20, 1998.

This invention relates to a single-stage process for the production of α-hydroxy ethers by oxidation of C=C unsaturated compounds with hydroperoxides in the presence of a mono- or polyhydric alcohol as a nucleophile and solvent, wherein systems based on molybdenum compounds with boron trifluoride or alumina or 1,8-diazabicyclo-[5.4.0]-undec-7-ene or 1,4-diazabicyclo-[2.2.2]-octane are used an catalysts.

Industry has an interest in α-hydroxy ethers, for example those represented by formulae (I) and (II). The compounds according to formula (I) may be employed in cosmetics, as lubricants for synthetic resins, in emulsion paints, as solvents, and as surfactants or co-surfactants.

The compounds according to formula (II) belong to the group of gemini surfactants, such as those described in WO 96/16033. These compounds according to formula (II) either serve as precursors of the ionic and nonionic, amphiphilic compounds referred to in WO 96/16033, or may be used as emulsifiers, demulsifiers, auxiliaries in metal working, ore mining, or surface finishing, as textile auxiliaries, or for cleaning and washing textiles or hard surfaces, and for washing and cleaning skin and hair.

Formula (I)

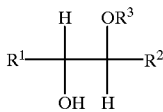

Formula (II)

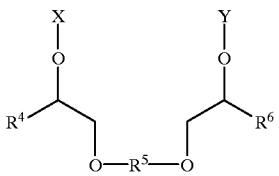

$R^1$, $R^2$, $R^4$, and $R^6$, independently of one another, are saturated, unbranched or branched hydrocarbon radicals, or are completely or partially fluorinated hydrocarbon radicals having 1 to 22 carbon atoms, preferably 8 to 18 carbon atoms. In detail, the radicals methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-henicosyl, n-docosyl, and the branched-chain isomers thereof or their completely or partially fluorinated hydrocarbon radicals are referred to herein.

$R^3$ represents mono- or polyhydric, linear or branched radicals of alcohols having 1 to 22 carbon atoms which may also be fluorinated wholly or in part. Examples include methanol, ethanol, n- and iso-propanol, n- and iso-butanol, pentanol, hexanol, heptanol, n-octanol, 2-ethyl hexanol, nonanol, decanol, undecanol, dodecanol, tridecanol, tetradecanol, pentadecanol, hexadecanol, heptadecanol, octadecanol, nonadecanol, eicosanol, heneicosanol, docosanol, ethylene glycol, diethylene glycol, triethylene glycol, 1,4-butanediol, trimethylol propane, neopentyl glycol, glycerol, and trifluoroethanol and mixtures thereof. Among long-chain alcohols, particularly those compounds with even carbon numbers are preferred. $R^5$ is a spacer consisting of an unbranched or branched chain with 2 to 100 carbon atoms which contains 0 to 20 oxygen atoms, 0 to 20 nitrogen atoms, 0 to 4 sulfur atoms, and 0 to 3 phosphorus atoms, and which has 0 to 20 functional side groups, such as hydroxyl, carbonyl, carboxyl, amino and/or acylamino groups. Said spacer is described in greater detail in WO 96/16033 incorporated by reference herein.

X and Y, independently of one another, are substituents according to formula XVI

where
α=0 to 50, preferably α=10 to 30,
β=0 to 60, preferably β=20 to 40,
and
α+β=1 to 100, preferably
α+β=10 to 50,
and wherein the alkoxide units are incorporated randomly or blockwise and the sequence is optional,
or are substituents according to formula XVII

where each
γ=0 to 20, preferably γ=0 to 8,
δ=0 to 20, preferably γ=0 to 12,
and
γ+δ=0 to 40, preferably
γ+δ=5 to 20,
and FR represents a functional radical
—$CH_2$—COOM, —$SO_3$M, —P(O(OM))$_2$,
—$C_3H_6$—$SO_3$M, or
—O—C(O)—$C_2H_3$($SO_3$M)—$CO_2$M',
wherein M, M' are equal to alkali, ammonium, alkanol ammonium, or ½ alkaline earth metal.

In each case the degree of alkoxylation is a mean which, within the defined limits, can be any value, including a non-integral one.

Prior-art processes for the production of said hydroxy ethers from olefins comprise two stages. At first, the olefin is epoxidized with a suitable oxidant and then purified. Per-acids are employed as oxidants for the epoxidation of long-chain olefins. Using silver catalysts, ethylene and butadiene can directly be reacted with oxygen to yield the corresponding epoxides. The customary method for producing propylene oxide is by molybdenum-, vanadium-, or titanium-catalyzed epoxidation of propylene with hydroperoxides. Although it is well known from literature that long-chain epoxides, too, can be epoxidized by the so-called Halcon (or oxirane) process [for example, cf. R. A. Sheldon, *J. Mol. Catal.*, 7 (1980), 107], said process has not been employed hitherto for this purpose. In the second stage of the process for producing α-hydroxy ethers the epoxides are opened with an alcohol usually in the presence of a catalyst. Since epoxides are rather expensive, they are rarely utilized for industrial processes. Thus, there remained a pressing need for a process which does not require expensive raw materials and wherein the epoxide stage occurs as an intermediate stage.

The opening of the oxirane ring is fairly easy with short-chain epoxides, such as ethylene oxide or propylene oxide, but requires ever-severer reaction conditions with increasing chain lengths. Both acids and bases are suitable as catalysts. In practice, classical Brønsted acids, such as $H_2SO_4$ [see R. A. Wohl, *Chimie*, 28 (1974) 1; DE 38 29 735], a large number of different Lewis acids [see e.g. P. Gassmann, T. Guggenheim, *J. Am. Chem. Soc.*, 104 (1982) 5849; M. Bischoff, U. Zeidler, H. Baumann, *Fette, Seifen, Anstrichmittel*, 79 (1979) 131], heteropolyacids [see e.g. Y. Izumi, K. Hayashi, *Chem. Lett.* (1980) 787], and $Al_2O_3$ [cf. G. H. Posner, *Angew. Chem.*, 90 (1978) 527] as well as sulfuric acid-treated phyllosilicates [cf. S. Hellbardt, K. Schlandt, W. H. Zech, DE 42 03 077] have been employed. However, the latter ones require significantly higher temperatures (>130° C.).

There are only few experiments known from literature which describe the production of α-hydroxy ethers from olefins by a single-stage synthesis. U.S. Pat. No. 2,808,442 describes the wolfram-catalyzed direct synthesis of α-hydroxy ethers by reaction with a 35% to 100% hydrogen peroxide. The water which is inevitably present results in the formation of vicinal diols. Therefore, when using a 35% hydrogen peroxide, the α-hydroxy ethers are defined as mere by-products. Titanium silicalites, too, have been used as catalysts for the direct synthesis of α-hydroxy ethers from olefins and alcohols using hydrogen peroxide (cf. GB 2 252 556), but the problem of competing ring opening due to the presence of water persists.

Hence, it is the object of the present invention to develop a process for the direct, single-stage production of α-hydroxy ethers which process is carried out in the absence of water, thus preventing the competing production of diol which is regarded as the main disadvantage of the processes described hereinabove.

According to the present invention, the problem is solved by using
- organic hydroperoxides, ROOH, as oxidants
- homogeneous or heterogeneous molybdenum compounds as a first catalyst component
- boron trifluoride in the form of a stabilized complex, or an alumina, or 1,8-diazabicyclo-[5.4.0]-un-dec-7-ene, or 1,4-diazabicyclo-[2.2.2]-octane as a second catalyst component
- mono- or polyhydric alcohols as nucleophiles and, simultaneously, as solvents without precluding the use of other solvents.

Therefore, the subject matter of the present invention is a single-stage process for the production of α-hydroxy ethers according to formulae (I) and (II) which process is performed by the oxidation of olefinic substrates with organic hydroperoxides and opening of the resultant oxirane ring using mono- or polyhydric alcohols, characterized in that molybdenum compounds in combination with boron trifluoride or alumina or 1,8-diazabicyclo-[5.4.0]-undec-7-ene or 1,4-diazabicyclo-[2.2.2]-octane are employed as a catalyst system.

Examples of alumina, $Al_2O_3$, particularly include α-$Al_2O_3$ (corundum), γ-$Al_2O_3$, or hydrates, such as α-$Al_2O_3.H_2O$ (diaspore), γ-$Al_2O_3$ (boehmite), $Al_2O_3$.3 $H_2O$ (hydrargillite), or $Al_2O_3$.3 $H_2O$ (bayerite).

Although each of the reaction components is known, it is surprising that they can be combined in a single-stage process wherein the reaction selectively yields the α-hydroxy ether. The catalyst components do not have any adverse effects on each other. On the contrary, it has been found that $BF_3$ enhances the activity of the molybdenum catalyst for epoxidation.

According to the process of the present invention, suitable catalyst components for the epoxidation are molybdenum compounds which are either soluble in the reaction mixture, e.g. molybdenyl acetylacetonate, $MoO_2(acac)_2$, or molybdenum hexacarbonyl, $Mo(CO)_6$, or molybdenum oxide on a support as a heterogeneous catalyst. Suitable catalyst supports are amorphous alumino-silicates or zeolites with high Lewis acidity. The molybdenum catalyst is employed in quantities of 0.01 to 5 mole %, preferably 0.25 to 2 mole %, most preferably 0.5 to 1.0 mole %, relative to the C=C double bond to be oxidized.

Boron trifluoride or adducts, such as etherate or methanolate, may be employed as the second catalyst component according to the instant invention. Further examples include alumina, $Al_2O_3$, the basic compound 1,8-diazabicyclo-[5.4.0]-undec-7-ene, and 1,4-diazabicyclo-[2.2.2]-octane which are used in quantities of 0.01 to 5 mole %, preferably 0.25 to 2.0 mole %, most preferably 0.5 to 1.0 mole %, based on the C=C double bond to be oxidized.

Suitable olefinic substrates are terminal and/or internal, singly or multiply unsaturated aliphatic, cyclic, or acyclic hydrocarbons, such as di- and trimers of butene or tri- and tetramers of propene, or unsaturated fatty acids and the esters thereof. Expediently, the alcohol component of the fatty acid esters should be identical with the alcohol employed in order that the likewise catalyzed transesterification does not result in undesirable product mixtures.

Mono- or polyhydric alcohols with primary, secondary, or tertiary hydroxyl groups and optional chain lengths may be used in the process of the present invention. For the production of compounds according to formula (II) it is desirable to use only primary hydroxyl groups for the etherification so that undesirable product mixtures are avoided. The alcohol and the olefinic substrate may contain additional functional groups, such as ester groups, carbonyl carbons, amides, ethers, provided that these groups do not interfere as nucleophiles during the reaction.

Suitable oxidants for the process of the present invention are commercially available hydroperoxides, such as tert-butyl hydroperoxide or cumene hydroperoxide, which are employed in proportions of 1.0 to 1.3, based on the double bond equivalents to be oxidized.

The reaction according to the process of the present invention can be carried out at any temperature ranging from the melting point to the boiling point of the reaction mixture. For safety reasons, a temperature of 100° C. should not be exceeded. Furthermore, the reaction is carried out in an inert gas atmosphere and with dehydrated reactants. The reaction is initiated by mixing catalyst components and alcohol plus olefin and heating this mixture to reaction temperature. Then, the hydroperoxide is slowly added. Once the reaction is terminated, the catalyst components can be filtered off and further utilized if both are heterogeneous, which is the simplest case, or they have to be eliminated from the product by means of water. The α-hydroxy ethers thus produced can be purified by distillation if desired.

The present invention will now be described with reference to the following non-limiting examples.

EXAMPLES

1. Preparation of 8-butoxy-7-tetradecanol

7-Tetradecene (0.03 mole; 5.9 g) and $MoO_2(acac)_2$ (0.3 mmol; 98 mg) were dissolved in anhydrous 1-butanol (30 ml). There was then added one spatulaful of dry mole sieve (4 Å) followed by heating to 90° C. There was added 0.05 ml of $BF_3$ etherate (≈0.3 mmol) followed by the dropwise addition of anhydrous tert-butyl hydroperoxide (0.036 mole; 3M in decane, 12 ml) in 30 minutes. The mixture was allowed to afterreact for 16 hours. The product then was cooled, acidified with dilute hydrochloric acid and taken up in ether. The organic phase was washed with water. The resultant crude product was dried over $Na_2SO_4$ and analyzed by gas chromatographic techniques. It was found to contain 8-butoxy-7-tetradecanol as a main product, but also 7,8-tetradecanediol, 7,8-epoxytetradecane, and unreacted 7-tetradecene. After addition of a GC standard (heptanoic acid ethyl ester) and conversion of the free carboxylic acids with $CH_2N_2$ to yield the corresponding methyl esters, the quantities of products were determined, while taking into account the respective response factors which had previously been determined from pure substances.

| | |
|---|---|
| 8-Butoxy-7-tetradecanol yield | 60% of theoretical* |
| 7,8-Tetradecanediol yield | 2% of theoretical* |
| 7,8-Epoxytetradecane yield | 2% of theoretical* |
| 7-Tetradecene conversion | 65% |

*relative to 7-tetradecene

2. Preparation of 8-(2-butoxy)-7-tetradecanol

Example 1 was repeated, the difference being that anhydrous 2-butanol (30 ml) was employed and the afterreaction period was 48 hours. According to GC analysis, the 8-(2-butoxy)-7-tetradecanol yield was 55% of theoretical, relative to 7-tetradecene.

3. Preparation of 8-(tert-butoxy)-7-tetradecanol

Example 1 was repeated, the difference being that anhydrous tert-butanol (30 ml) was employed and the afterreaction period was 48 hours. According to GC analysis, the 8-(tert-butoxy)-7-tetradecanol yield was 48% of theoretical, relative to 7-tetradecene.

4. Preparation of 8-hexoxy-7-tetradecanol

Example 1 was repeated, the difference being that anhydrous 1-hexanol (30 ml) was employed. The afterreaction period was 16 hours. According to GC analysis, the 8-hexoxy-7-tetradecanol yield was 58% of theoretical, relative to 7-tetradecene.

5. Preparation of 2-butoxy-1-tetradecanol/1-butoxy-2-tetradecanol

Example 1 was repeated, the difference being that 1-tetradecene (0.03 mole; 5.9 g) was employed and the afterreaction period was 48 hours. According to GC analysis, the 2-butoxy-1-tetradecanol/1-butoxy-2-tetradecanol yield was 64% of theoretical, relative to 7-tetradecene.

6. Preparation of 2-butoxy-cyclohexanol

Cyclohexene (0.05 mole; 4.1 g) and $MoO_2(acac)_2$ (0.5 mmol; 162 mg) were dissolved in anhydrous 1-butanol (30 ml). There was then added one spatulaful of dry mole sieve (4 Å) followed by heating to 60° C. There was added 0.08 ml of $BF_3$ etherate (≈0.5 mmol) followed by the dropwise addition of anhydrous tert-butyl hydroperoxide (0.06 mole; 3M in decane, 20 ml) in 30 minutes. The mixture was allowed to afterreact for 16 hours. The product then was further treated as described in Example 1. According to GC analysis, the 2-butoxy-cyclohexanol yield was 53% of theoretical, relative to cyclohexene.

7. Preparation of 7-butoxy-8-hydroxy-octadecanoic acid-(butyl ester) and 8-butoxy-7-hydroxy-octadecanoic acid-(butyl ester)

Example 1 was repeated, the difference being that oleic acid (0.03 mole; 9.6 g; 88%) was used. After esterification of the free carboxylic acids with $CH_2N_2$, the following yields were found by GC analysis: 7-butoxy-8-hydroxy-octadecanoic acid butyl ester/8-butoxy-7-hydroxy-octadecanoic acid butyl ester: 37% of theoretical, relative to oleic acid; 7-butoxy-8-hydroxy-octadecanoic acid butyl ester/8-butoxy-7-hydroxy-octadecanoic acid butyl ester: 33% of theoretical, relative to oleic acid.

8. Preparation of 7-methoxy-8-hydroxy-octadecanoic acid methyl ester and 8-methoxy-7-hydroxy-octadecanoic acid methyl ester Example 1 was repeated, the difference being that oleic acid methyl ester (0.03 mole; 10.5 g; 85%) and anhydrous methanol (30 ml) were used at 65° C. According to GC analysis, the 7-methoxy-8-hydroxy-octadecanoic acid methyl ester/8-methoxy-7-hydroxy-octadecanoic acid methyl ester yield was 65% of theoretical, relative to oleic acid.

9. Preparation of 8-(4-hydroxybutoxy)-7-tetradecanol

Example 1 was repeated, the difference being that anhydrous 1,4-butanediol (100 ml) was used. The afterreaction period was 16 hours. According to GC analysis, the 8-(4-hydroxybutoxy)-7-tetradecanol yield was 58% of theoretical, relative to 7-tetradecene.

10. Preparation of 8-trifluoroethoxy-7-tetradecanol

Example 1 was repeated, the difference being that trifluoroethanol (20 ml) was used. The afterreaction period was 16 hours. According to GC analysis, the 8-trifluoroethoxy-7-tetradecanol yield was 70% of theoretical, relative to 7-tetradecene.

11. Preparation of 8-(2-methoxyethoxy)-7-tetradecanol

Example 1 was repeated, the difference being that anhydrous ethylene glycol monomethyl ether (30 ml) was used. The afterreaction period was 16 hours. According to GC analysis, the 8-(2-methoxyethoxy)-7-tetradecanol yield was 54% of theoretical, relative to 7-tetradecene.

12. Preparation of 8-butoxy-7-tetradecanol

Example 1 was repeated, the difference being that $Mo(CO)_6$ (0.3 mmol, 79 mg) was used. The afterreaction period was 16 hours. According to GC analysis, the 8-butoxy-7-tetradecanol yield was 63% of theoretical, relative to 7-tetradecene.

13. Preparation of 8-butoxy-7-tetradecanol

Example 1 was repeated, the difference being that cumene hydroperoxide (0.036 mole; 6.9 g; 80%) was used. The afterreaction period was 16 hours. According to GC analysis, the 8-butoxy-7-tetradecanol yield was 50% of theoretical, relative to 7-tetradecene.

14. Preparation of 8-butoxy-7-tetradecanol

Example 1 was repeated, the difference being that a heterogeneous molybdenum catalyst (nominally 0.3 mmol Mo; 2.9 g) was used which had been prepared as follows:

An amorphous alumino-silicate containing 20 wt. % $SiO_2$ was calcined at 550° C. for 16 hours under a stream of air. Then, 38.4 g of this support material in 500 ml of 1,4-dioxane/water (9:1) were impregnated over night at boiling temperature with 4 mmol of $MoO_2(acac)_2$. After this period the solvent was removed using a rotary evaporator. The impregnated catalyst then was activated at 550° C. under a stream of air and was finally filtered off. According to GC analysis, the following yields were found:

| | |
|---|---|
| 8-Butoxy-7-tetradecanol: | 66% of theoretical* |
| 7,8-Tetradecanediol: | 2% of theoretical* |
| 7,8-Epoxytetradecane: | 18% of theoretical* |

*relative to 7-tetradecene

The 7-tetradecene conversion was 94%.

What is claimed is:

1. A single-stage process for the production of α-hydroxy ethers according to formulae (I) and (II)

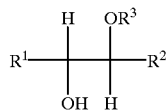

Formula (I)

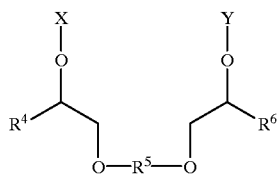

Formula (II)

by oxidation of olefinic substrates with organic hydroperoxides and opening of the resultant oxirane ring by mono- or polyhydric alcohols, wherein molybdenum compounds in combination with a compound selected from the group consisting of boron trifluoride, alumina, 1,8-diazabicyclo-[5.4.0]-undec-7-ene, 1,4-diazabicyclo-[2.2.2]-octane and mixtures thereof are used as a catalyst system and a catalyst support selected from the group consisting of amorphous alumino-silicates and zeolites is used, and wherein $R^1$, $R^2$, $R^4$, and $R^6$, independently of one another, are saturated, unbranched or branched hydrocarbon radicals having 1 to 22 carbon atoms, or are completely or partially fluorinated hydrocarbon radicals having 1 to 22 carbon atoms, $R^3$ represents a mono- or polyhydric, linear or branched radical of an alcohol having 1 to 22 carbon atoms which may be fluorinated wholly or in part, $R^5$ is spacer consisting of an unbranched or branched chain with 2 to 100 carbon atoms which contains 0 to 20 oxygen atoms, 0 to 20 nitrogen atoms, 0 to 4 sulfur atoms, and 0 and 3 phosphorus atoms and which has 0 to 20 hydroxyl, carbonyl, carboxyl, amino and/or acylamino groups, and X and Y, independently of one another, are substituents according to formula XVI $$-(C_2H_4O)_\alpha(C_3H_6O)_\beta H \qquad (XVI)$$

where $\alpha = 0$ to $50$ $\beta = 0$ to $60$ and $\alpha + \beta = 1$ to $100$ and wherein the alkoxide are incorporated randomly or blockwise and the sequence is optional, or are substituents according to formula XVII $$-(C_2H_4O)_\gamma(C_3H_6O)_\delta\text{-FR} \qquad (XVII)$$

where each $\gamma = 0$ to $20$ $\delta = 0$ to $20$ and $\gamma + \delta = 0$ to $40$ and FR represents a functional radical

—$CH_2$—COOM, —$SO_3M$, —$P(O)(OM)_2$,

—$C_3H_6$—$SO_3M$, or

—O—C(O)—$C_2H_3(SO_3M)$—$CO_2M'$, wherein M, M' are equal to alkali, ammonium, alkanol ammonium or ½ alkaline earth metal, and the alkoxide units, too, are incorporated randomly or blockwise and the sequence is optional.

* * * * *

UNITED STATES PATENT AND TRADEMARK OFFICE
CERTIFICATE OF CORRECTION

PATENT NO.   : 6,380,439 B1
DATED        : April 30, 2002
INVENTOR(S)  : Mark Ruschgen Klass et al.

It is certified that error appears in the above-identified patent and that said Letters Patent is hereby corrected as shown below:

Column 8,
Line 22, add the word -- units -- after the word "alkoxide"

Signed and Sealed this

Eighteenth Day of March, 2003

JAMES E. ROGAN
*Director of the United States Patent and Trademark Office*